US012642586B2

(12) United States Patent     (10) Patent No.:   US 12,642,586 B2

De Marchena     (45) Date of Patent:   *Jun. 2, 2026

(54) TRANSAPICAL REMOVAL DEVICE

(71) Applicant: EVALVE, INC., Santa Clara, CA (US)

(72) Inventor: Eduardo De Marchena, Miami, FL (US)

(73) Assignee: Evalve, Inc., Santa Clara, CA (US)

( * ) Notice: Subject to any disclaimer, the term of this patent is extended or adjusted under 35 U.S.C. 154(b) by 353 days.

This patent is subject to a terminal disclaimer.

(21) Appl. No.: 18/448,629

(22) Filed: Aug. 11, 2023

(65) Prior Publication Data

US 2023/0380900 A1    Nov. 30, 2023

Related U.S. Application Data

(63) Continuation of application No. 16/311,529, filed as application No. PCT/US2017/038309 on Jun. 20, 2017, now Pat. No. 11,963,712.

(Continued)

(51) Int. Cl.
   *A61B 18/14*      (2006.01)
   *A61B 17/128*     (2006.01)
        (Continued)

(52) U.S. Cl.
   CPC ...... *A61B 18/1492* (2013.01); *A61B 17/1285* (2013.01); *A61B 17/22* (2013.01);
        (Continued)

(58) Field of Classification Search
   CPC . A61B 18/1492; A61B 17/1285; A61B 17/22; A61B 17/22031; A61B 17/221;
        (Continued)

(56) References Cited

U.S. PATENT DOCUMENTS

| | | |
|---|---|---|
| 3,378,010 A | 4/1968 | Codling |
| 3,470,875 A | 10/1969 | Johnson |

(Continued)

FOREIGN PATENT DOCUMENTS

| | | |
|---|---|---|
| CA | 2296317 C | 1/2009 |
| DE | 9100873 U1 | 4/1991 |

(Continued)

OTHER PUBLICATIONS

Dang et al., "Surgical Revision After Percutaneous Mitral Valve Repair With a Clip: Initial Multicenter Experience," Ann Thorac Surg 80:2338-2342 (2005).

(Continued)

*Primary Examiner* — Aaron F Roane

(74) *Attorney, Agent, or Firm* — Honigman LLP; Brett A. Krueger

(57) ABSTRACT

A transapical removal device that can be deployed in a catheter procedure to capture for removal or alteration a mitral valve clip or heart tissue, such as the anterior leaflet of the mitral valve, and methods of use are disclosed. The removal device includes a delivery catheter configured to be deployed near a mitral valve using a guide catheter. The delivery catheter has a snare head at the distal end, which assumes a collapsed state during movement of the delivery catheter through the guide catheter and deployed state for capturing a mitral valve clip or anterior leaflet. The snare head has one or more ablation delivery catheters configured to ablate tissue surrounding the pre-positioned mitral valve clip or anterior leaflet. In some arrangements within the scope of the present disclosure, the removal device includes a deployment mechanism for deploying a new transcatheter valve into the mitral valve.

21 Claims, 12 Drawing Sheets

Related U.S. Application Data

(60) Provisional application No. 62/352,235, filed on Jun. 20, 2016.

(51) Int. Cl.

| | |
|---|---|
| *A61B 17/22* | (2006.01) |
| *A61B 17/221* | (2006.01) |
| *A61B 17/32* | (2006.01) |
| *A61B 17/34* | (2006.01) |
| *A61B 17/50* | (2006.01) |
| *A61B 18/02* | (2006.01) |
| *A61B 18/24* | (2006.01) |
| *A61B 17/00* | (2006.01) |
| *A61B 18/00* | (2006.01) |
| *A61B 18/12* | (2006.01) |

(52) U.S. Cl.

CPC ...... *A61B 17/22031* (2013.01); *A61B 17/221* (2013.01); *A61B 17/32* (2013.01); *A61B 17/34* (2013.01); *A61B 17/50* (2013.01); *A61B 18/02* (2013.01); *A61B 18/1445* (2013.01); *A61B 18/24* (2013.01); *A61B 2017/00243* (2013.01); *A61B 2017/00318* (2013.01); *A61B 2017/00358* (2013.01); *A61B 2017/00876* (2013.01); *A61B 2017/22035* (2013.01); *A61B 2017/22097* (2013.01); *A61B 2017/2215* (2013.01); *A61B 2018/00267* (2013.01); *A61B 2018/00273* (2013.01); *A61B 2018/00369* (2013.01); *A61B 2018/00577* (2013.01); *A61B 2018/0212* (2013.01); *A61B 2018/1226* (2013.01)

(58) Field of Classification Search

CPC ......... A61B 17/32; A61B 17/34; A61B 17/50; A61B 18/02; A61B 18/1445; A61B 18/24; A61B 2017/00243; A61B 2017/00318; A61B 2017/00358; A61B 2017/00876; A61B 2017/22035; A61B 2017/22097; A61B 2017/2215; A61B 2018/00267; A61B 2018/00273; A61B 2018/00369; A61B 2018/00577; A61B 2018/0212; A61B 2018/1226

USPC ......................................................... 607/119

See application file for complete search history.

(56) References Cited

U.S. PATENT DOCUMENTS

| | | | |
|---|---|---|---|
| 3,874,388 A | 4/1975 | King |
| 4,007,743 A | 2/1977 | Blake |
| 4,055,861 A | 11/1977 | Carpentier |
| 4,312,337 A | 1/1982 | Donohue |
| 4,327,736 A | 5/1982 | Inoue |
| 4,340,091 A | 7/1982 | Skelton |
| 4,646,719 A | 3/1987 | Neuman |
| 4,657,024 A | 4/1987 | Coneys |
| 4,693,248 A | 9/1987 | Failla |
| 4,716,886 A | 1/1988 | Schulman |
| 4,795,458 A | 1/1989 | Regan |
| 4,809,695 A | 3/1989 | Gwathmey |
| 4,930,674 A | 6/1990 | Barak |
| 4,998,917 A | 3/1991 | Gaiser |
| 5,002,562 A | 3/1991 | Oberlander |
| 5,069,679 A | 12/1991 | Taheri |
| 5,071,428 A | 12/1991 | Chin |
| 5,098,440 A | 3/1992 | Hillstead |
| 5,125,895 A | 6/1992 | Buchbinder |
| 5,147,370 A | 9/1992 | McNamara |
| 5,171,259 A | 12/1992 | Inoue |
| 5,217,460 A | 6/1993 | Knoepfler |

| | | | |
|---|---|---|---|
| 5,222,963 A | 6/1993 | Brinkerhoff |
| 5,238,002 A | 8/1993 | Devlin |
| 5,271,544 A | 12/1993 | Fox |
| 5,327,905 A | 7/1994 | Avitall |
| 5,330,501 A | 7/1994 | Tovey |
| 5,334,217 A | 8/1994 | Das |
| 5,363,861 A | 11/1994 | Edwards |
| 5,389,077 A | 2/1995 | Melinyshyn |
| 5,403,326 A | 4/1995 | Harrison |
| 5,425,744 A | 6/1995 | Fagan |
| 5,450,860 A | 9/1995 | O'Connor |
| 5,452,837 A | 9/1995 | Williamson, IV |
| 5,456,400 A | 10/1995 | Shichman |
| 5,456,674 A | 10/1995 | Bos |
| 5,478,353 A | 12/1995 | Yoon |
| 5,542,949 A | 8/1996 | Yoon |
| 5,562,678 A | 10/1996 | Booker |
| 5,601,224 A | 2/1997 | Bishop |
| 5,601,574 A | 2/1997 | Stefanchik |
| 5,607,462 A | 3/1997 | Imran |
| 5,607,471 A | 3/1997 | Seguin |
| 5,609,598 A | 3/1997 | Laufer |
| 5,611,794 A | 3/1997 | Sauer |
| 5,636,634 A | 6/1997 | Kordis |
| 5,695,504 A | 12/1997 | Gifford, III |
| 5,713,911 A | 2/1998 | Racenet |
| 5,716,417 A | 2/1998 | Girard |
| 5,741,297 A | 4/1998 | Simon |
| 5,755,778 A | 5/1998 | Kleshinski |
| 5,782,239 A | 7/1998 | Webster, Jr. |
| 5,797,960 A | 8/1998 | Stevens |
| 5,810,847 A | 9/1998 | Laufer |
| 5,814,097 A | 9/1998 | Sterman |
| 5,820,630 A | 10/1998 | Lind |
| 5,843,178 A | 12/1998 | Vanney |
| 5,849,019 A | 12/1998 | Yoon |
| 5,855,601 A | 1/1999 | Bessler |
| 5,908,420 A | 6/1999 | Parins |
| 5,976,159 A | 11/1999 | Bolduc |
| 6,015,417 A | 1/2000 | Reynolds, Jr. |
| 6,048,351 A | 4/2000 | Gordon |
| 6,079,414 A | 6/2000 | Roth |
| 6,117,144 A | 9/2000 | Nobles |
| 6,120,496 A | 9/2000 | Whayne |
| 6,139,508 A | 10/2000 | Simpson |
| 6,149,658 A | 11/2000 | Gardiner |
| 6,165,183 A | 12/2000 | Kuehn |
| 6,182,664 B1 | 2/2001 | Cosgrove |
| 6,193,734 B1 | 2/2001 | Bolduc |
| 6,200,315 B1 | 3/2001 | Gaiser |
| 6,217,528 B1 | 4/2001 | Koblish |
| 6,269,819 B1 | 8/2001 | Oz |
| 6,290,674 B1 | 9/2001 | Roue |
| 6,312,447 B1 | 11/2001 | Grimes |
| 6,332,880 B1 | 12/2001 | Yang |
| 6,334,860 B1 | 1/2002 | Dorn |
| 6,346,074 B1 | 2/2002 | Roth |
| 6,419,640 B1 | 7/2002 | Taylor |
| 6,419,696 B1 | 7/2002 | Ortiz |
| 6,461,366 B1 | 10/2002 | Seguin |
| 6,471,702 B1 | 10/2002 | Goto |
| 6,482,224 B1 | 11/2002 | Michler |
| 6,496,420 B2 | 12/2002 | Manning |
| 6,540,719 B2 | 4/2003 | Bigus |
| 6,544,215 B1 | 4/2003 | Bencini |
| 6,551,303 B1 | 4/2003 | Van Tassel |
| 6,575,971 B2 | 6/2003 | Hauck |
| 6,599,311 B1 | 7/2003 | Biggs |
| 6,626,930 B1 | 9/2003 | Allen |
| 6,629,534 B1 | 10/2003 | St Goar |
| 6,669,687 B1 | 12/2003 | Saadat |
| 6,695,866 B1 | 2/2004 | Kuehn |
| 6,719,767 B1 | 4/2004 | Kimblad |
| 6,752,813 B2 | 6/2004 | Goldfarb |
| 6,770,083 B2 | 8/2004 | Seguin |
| 6,797,002 B2 | 9/2004 | Spence |
| 6,837,867 B2 | 1/2005 | Kortelling |
| 6,855,137 B2 | 2/2005 | Bon |
| 6,875,224 B2 | 4/2005 | Grimes |

(56) References Cited

U.S. PATENT DOCUMENTS

| | | | |
|---|---|---|---|
| 6,908,481 | B2 | 6/2005 | Cribier |
| 6,926,730 | B1 | 8/2005 | Nguyen |
| 6,932,810 | B2 | 8/2005 | Ryan |
| 7,011,669 | B2 | 3/2006 | Kimblad |
| 7,101,395 | B2 | 9/2006 | Tremulis |
| 7,112,207 | B2 | 9/2006 | Allen |
| 7,125,421 | B2 | 10/2006 | Tremulis |
| 7,226,467 | B2 | 6/2007 | Lucatero |
| 7,338,467 | B2 | 3/2008 | Lutter |
| 7,556,632 | B2 | 7/2009 | Zadno |
| 7,563,267 | B2 | 7/2009 | Goldfarb |
| 7,569,062 | B1 | 8/2009 | Kuehn |
| 7,604,646 | B2 | 10/2009 | Goldfarb |
| 7,635,329 | B2 | 12/2009 | Goldfarb |
| 7,655,015 | B2 | 2/2010 | Goldfarb |
| 7,666,204 | B2 | 2/2010 | Thornton |
| 7,736,388 | B2 | 6/2010 | Goldfarb |
| 7,811,296 | B2 | 10/2010 | Goldfarb |
| 7,972,323 | B1 | 7/2011 | Bencini |
| 7,981,139 | B2 | 7/2011 | Martin |
| 8,057,493 | B2 | 11/2011 | Goldfarb |
| 8,062,313 | B2 | 11/2011 | Kimblad |
| 8,118,822 | B2 | 2/2012 | Schaller |
| 8,216,230 | B2 | 7/2012 | Hauck |
| 8,216,256 | B2 | 7/2012 | Raschdorf, Jr. |
| 8,303,608 | B2 | 11/2012 | Goldfarb |
| 8,500,761 | B2 | 8/2013 | Goldfarb |
| 8,623,077 | B2 | 1/2014 | Cohn |
| 8,702,701 | B2 | 4/2014 | Suzuki |
| 8,734,505 | B2 | 5/2014 | Goldfarb |
| 8,740,920 | B2 | 6/2014 | Goldfarb |
| 8,821,518 | B2 | 9/2014 | Saliman |
| 8,870,948 | B1 | 10/2014 | Erzberger |
| 9,211,119 | B2 | 12/2015 | Hendricksen |
| 9,439,757 | B2 | 9/2016 | Wallace |
| 9,510,829 | B2 | 12/2016 | Goldfarb |
| 9,770,256 | B2 | 9/2017 | Cohen |
| 10,076,415 | B1 | 9/2018 | Metchik |
| 10,105,222 | B1 | 10/2018 | Metchik |
| 10,123,873 | B1 | 11/2018 | Metchik |
| 10,130,475 | B1 | 11/2018 | Metchik |
| 10,136,993 | B1 | 11/2018 | Metchik |
| 10,159,570 | B1 | 12/2018 | Metchik |
| 10,231,837 | B1 | 3/2019 | Metchik |
| 10,238,493 | B1 | 3/2019 | Metchik |
| 10,245,144 | B1 | 4/2019 | Metchik |
| 10,258,408 | B2 | 4/2019 | Fung |
| D847,983 | S | 5/2019 | Ho |
| 10,314,586 | B2 | 6/2019 | Greenberg |
| 10,413,408 | B2 | 9/2019 | Krone |
| 10,470,881 | B2 | 11/2019 | Noe |
| 10,507,109 | B2 | 12/2019 | Metchik |
| 10,517,726 | B2 | 12/2019 | Chau |
| 10,524,792 | B2 | 1/2020 | Hernandez |
| 10,595,997 | B2 | 3/2020 | Metchik |
| 10,624,664 | B2 | 4/2020 | Cohen |
| 10,631,893 | B2 | 4/2020 | Drapeau |
| 10,646,342 | B1 | 5/2020 | Marr |
| 10,736,632 | B2 | 8/2020 | Khairkhahan |
| 10,751,173 | B2 | 8/2020 | Morriss |
| 10,779,837 | B2 | 9/2020 | Lee |
| D902,403 | S | 11/2020 | Marsot |
| 10,856,988 | B2 | 12/2020 | Mcniven |
| 11,602,367 | B2 | 3/2023 | Cohen |
| 2002/0013571 | A1 | 1/2002 | Goldfarb |
| 2002/0183787 | A1 | 12/2002 | Wahr |
| 2003/0069593 | A1 | 4/2003 | Tremulis |
| 2003/0167071 | A1 | 9/2003 | Martin |
| 2004/0034365 | A1 | 2/2004 | Lentz |
| 2004/0044350 | A1 | 3/2004 | Martin |
| 2004/0116951 | A1 | 6/2004 | Rosengart |
| 2005/0159763 | A1 | 7/2005 | Mollenauer |
| 2005/0192633 | A1 | 9/2005 | Montpetit |
| 2005/0267493 | A1 | 12/2005 | Schreck |
| 2006/0074484 | A1 | 4/2006 | Huber |
| 2006/0184198 | A1 | 8/2006 | Bales |
| 2007/0038293 | A1 | 2/2007 | Frederick |
| 2007/0213735 | A1 | 9/2007 | Saadat |
| 2008/0009858 | A1 | 1/2008 | Rizvi |
| 2008/0097467 | A1 | 4/2008 | Gruber |
| 2008/0140189 | A1 | 6/2008 | Nguyen |
| 2009/0012538 | A1 | 1/2009 | Saliman |
| 2009/0082857 | A1 | 3/2009 | Lashinski |
| 2009/0209955 | A1 | 8/2009 | Forster |
| 2009/0209991 | A1 | 8/2009 | Hinchliffe |
| 2010/0268226 | A1 | 10/2010 | Epp |
| 2011/0009864 | A1 | 1/2011 | Bucciaglia |
| 2011/0178366 | A1 | 7/2011 | Suzuki |
| 2011/0184405 | A1 | 7/2011 | Mueller |
| 2011/0238052 | A1 | 9/2011 | Robinson |
| 2012/0022527 | A1 | 1/2012 | Woodruff |
| 2013/0197299 | A1 | 8/2013 | Chin |
| 2014/0046320 | A1 | 2/2014 | Kappel |
| 2014/0228871 | A1* | 8/2014 | Cohen .............. A61B 17/32053 |
| | | | 606/170 |
| 2015/0238729 | A1 | 8/2015 | Jenson |
| 2015/0257883 | A1 | 9/2015 | Basude |
| 2017/0042546 | A1 | 2/2017 | Goldfarb |
| 2017/0049455 | A1 | 2/2017 | Seguin |
| 2017/0100250 | A1 | 4/2017 | Marsot |
| 2017/0239048 | A1 | 8/2017 | Goldfarb |
| 2017/0265994 | A1 | 9/2017 | Krone |
| 2018/0021133 | A1 | 1/2018 | Barbarino |
| 2018/0036119 | A1 | 2/2018 | Wei |
| 2018/0092661 | A1 | 4/2018 | Prabhu |
| 2018/0146964 | A1 | 5/2018 | Garcia |
| 2018/0235657 | A1 | 8/2018 | Abunassar |
| 2018/0242976 | A1 | 8/2018 | Kizuka |
| 2018/0243086 | A1 | 8/2018 | Barbarino |
| 2018/0325671 | A1 | 11/2018 | Abunassar |
| 2018/0344460 | A1 | 12/2018 | Wei |
| 2018/0353181 | A1 | 12/2018 | Wei |
| 2018/0360457 | A1 | 12/2018 | Ellis |
| 2019/0053803 | A1 | 2/2019 | Ketai |
| 2019/0125536 | A1 | 5/2019 | Prabhu |
| 2019/0151041 | A1 | 5/2019 | Ho |
| 2019/0151089 | A1 | 5/2019 | Wei |
| 2019/0159899 | A1 | 5/2019 | Marsot |
| 2019/0167197 | A1 | 6/2019 | Abunassar |
| 2019/0183571 | A1 | 6/2019 | Eduardo |
| 2019/0209293 | A1 | 7/2019 | Metchik |
| 2019/0247187 | A1 | 8/2019 | Kizuka |
| 2019/0274831 | A1 | 9/2019 | Prabhu |
| 2019/0321597 | A1 | 10/2019 | Van Hoven |
| 2019/0343630 | A1 | 11/2019 | Kizuka |
| 2019/0350702 | A1 | 11/2019 | Hernandez |
| 2019/0350710 | A1 | 11/2019 | Ketai |
| 2019/0365536 | A1 | 12/2019 | Prabhu |
| 2020/0000473 | A1 | 1/2020 | Dell |
| 2020/0060687 | A1 | 2/2020 | Hernández |
| 2020/0078173 | A1 | 3/2020 | Mcniven |
| 2020/0113678 | A1 | 4/2020 | Mccann |
| 2020/0121460 | A1 | 4/2020 | Dale |
| 2020/0121894 | A1 | 4/2020 | Prabhu |
| 2020/0187942 | A1 | 6/2020 | Wei |
| 2020/0205829 | A1 | 7/2020 | Wei |
| 2020/0214733 | A1 | 7/2020 | Drapeau |
| 2020/0214764 | A1 | 7/2020 | Wilder |
| 2020/0245998 | A1 | 8/2020 | Basude |
| 2020/0261107 | A1 | 8/2020 | Cohen |
| 2020/0281591 | A1 | 9/2020 | Krone |
| 2020/0323528 | A1 | 10/2020 | Khairkhahan |
| 2020/0323549 | A1 | 10/2020 | Goldfarb |
| 2020/0323634 | A1 | 10/2020 | Von Oepen |
| 2020/0360018 | A1 | 11/2020 | Dell |
| 2020/0367871 | A1 | 11/2020 | Van Hoven |
| 2021/0137579 | A1 | 5/2021 | Rafiee |
| 2022/0361907 | A1 | 11/2022 | Osterbauer |

FOREIGN PATENT DOCUMENTS

| | | | |
|---|---|---|---|
| EP | 0558031 | B1 | 4/1999 |
| EP | 1383448 | A2 | 1/2004 |
| EP | 1383448 | B1 | 6/2008 |

(56)                    References Cited

FOREIGN PATENT DOCUMENTS

| | | | |
|---|---|---|---|
| EP | 2760351 | B1 | 5/2018 |
| FR | 2705556 | A1 | 12/1994 |
| FR | 2768324 | A1 | 3/1999 |
| FR | 2768325 | B1 | 11/1999 |
| JP | 2016508858 | A | 3/2016 |
| WO | 9101689 | A1 | 2/1991 |
| WO | 9212690 | A1 | 8/1992 |
| WO | 94018893 | A1 | 9/1994 |
| WO | 9508292 | A1 | 3/1995 |
| WO | 9632882 | A1 | 10/1996 |
| WO | 9727807 | A1 | 8/1997 |
| WO | 9807375 | A1 | 2/1998 |
| WO | 9907295 | A1 | 2/1999 |
| WO | 9907354 | A2 | 2/1999 |
| WO | 9913777 | A1 | 3/1999 |
| WO | 9915223 | A1 | 4/1999 |
| WO | 0003759 | A2 | 1/2000 |
| WO | 0060995 | A2 | 10/2000 |
| WO | 0128432 | A1 | 4/2001 |
| WO | 03020179 | A1 | 3/2003 |
| WO | 03049619 | A2 | 6/2003 |
| WO | 2015008286 | A1 | 1/2015 |
| WO | 2015057289 | A1 | 4/2015 |
| WO | 2016178722 | A1 | 11/2016 |
| WO | 2018093663 | A1 | 5/2018 |
| WO | 2019058178 | A1 | 3/2019 |
| WO | 2021007324 | A1 | 1/2021 |
| WO | 2021113785 | A1 | 6/2021 |

OTHER PUBLICATIONS

Rose et al., "Late MitraClip Failure: Removal Technique for Leaflet-Sparing Mitral Valve Repair," Journal of Cardiac Surgery 27:543-545 (2012).

* cited by examiner

FIG. 13

TRANSAPICAL REMOVAL DEVICE

CROSS-REFERENCE TO RELATED APPLICATION

This is a continuation of U.S. patent application Ser. No. 16/311,529, filed Dec. 19, 2018, which is a U.S. national stage of International Application No. PCT/US17/38309, filed Jun. 20, 2017, which claims the priority of U.S. Provisional Patent Application No. 62/352,235, filed Jun. 20, 2016, and entitled "Transapical Removal Device"; the entire contents thereof are incorporated by reference herein.

FIELD OF THE DISCLOSURE

This disclosure relates generally to a transapical removal device, and more specifically, to a transapcial removal device for removal of a mitral valve clip or the anterior leaflet of the mitral valve.

BACKGROUND

Mitral valve regurgitation occurs when a heart's mitral valve does not close tightly, allowing some blood to leak backward through the mitral valve into the atrium rather than flowing through the aortic valve. Mitral valve regurgitation is present in approximately 1.7% of the adult population, and the incidence rises with advancing age such that more than 9% of adults 75 years of age and older have moderate or severe mitral valve regurgitation. Because blood cannot move through the heart or to the rest of the body as efficiently in people suffering from mitral valve regurgitation, symptoms include shortness of breath and fatigue, as well as heart murmur, heart palpitations, and swollen feet or ankles. Severe mitral valve regurgitation can lead to heart failure, atrial fibrillation, and pulmonary hypertension. If left untreated, the one year mortality rate for mitral valve regurgitation is 57%.

A variety of treatment options have been developed to treat mitral valve regurgitation, including medications, open-heart surgery, and catheter procedures. One catheter procedure involves clipping together mitral valve leaflets of the mitral valve in order to improve the function of the mitral valve. Under certain circumstances, such as an allergic reaction, dislodgement of the clip, or infection, removal of a mitral valve clip is necessary. Unfortunately, after mitral valve clip deployment, the mitral valve clip can only be removed surgically, closing the door for future percutaneous mitral valve replacement and causing elevated morbidity and mortality. Preferably, removal of the mitral valve clip could be achieved by a catheter procedure that would not require open-heart surgery. Additionally, some patients with mitral valve regurgitation undergo transcatheter mitral valve replacement and subsequently experience a left ventricular outflow tract (LVOT) obstruction. The anterior mitral leaflets have been identified as playing a considerable role in the etiology of LVOT obstructions in many patients. Preferably, any catheter procedure for removing a mitral valve clip could also ablate, remove or modify the anterior mitral valve leaflets as a first step to transcatheter mitral valve replacement in order to prevent future complications, such as an LVOT obstruction.

SUMMARY OF THE DISCLOSURE

The current disclosure is directed to multiple arrangements of a transapical removal device that can be deployed in a catheter procedure to capture for removal or alteration a mitral valve clip or heart tissue, such as the anterior leaflet of the mitral valve, as well as to methods of use of such a transapical removal device. The removal device includes a delivery catheter configured to be deployed near a mitral valve using a guide catheter. In some arrangements, the guide catheter can be used to deploy the delivery catheter.

The delivery catheter has a snare head at the distal end, which assumes a collapsed state during movement of the delivery catheter along the guide catheter and a deployed state for capturing a mitral valve clip or anterior leaflet. The snare head controller controls the transition of the snare head between the collapsed and deployed states. The snare head has a snare basket for at least partially surrounding a pre-positioned mitral valve clip or the anterior leaflet. The snare basket may be made of, for example, medical-grade plastic, medical-grade metal, or both. The snare basket may be made of a shape memory material, such as nitinol, that assists in the transition from the collapsed state to the deployed state. In some arrangements, the snare head may comprise a spring that is compressed when the snare head is in the collapsed state and at rest when the snare head is in the deployed state, the spring configured to be compressed within the snare basket unless the snare basket is in the deployed state. A retraction funnel may be provided at a proximal end of the delivery catheter in order to forcibly return the snare head to the collapsed state from the deployed state. In some arrangements, magnets may be provided on the snare basket to facilitate closing the snare basket around the pre-positioned mitral valve clip or the anterior leaflet. In other arrangements, the snare basket may comprise a cord for cinching the snare basket around the pre-positioned mitral valve clip or the anterior leaflet.

In some arrangements, the snare basket may be a single-part basket having an oval shape. In other arrangements, the snare basket may be a two-part basket having a first basket side and a second basket side. The two-part basket may have a closed state, in which the first basket side and the second basket side are arranged to secure a mitral valve clip, tissue, or another element between them, and an open state, in which the first and second basket sides are separated from one another.

The snare head also has one or more ablation delivery catheters configured to ablate tissue surrounding the pre-positioned mitral valve clip or anterior leaflet. In some arrangements within the scope of the present disclosure, each ablation delivery catheter comprises an electrode for supplying radiofrequency energy to ablate tissue adjacent the mitral valve clip or anterior leaflet to allow for removal of the mitral valve clip or removal or alteration of the anterior leaflet. An electrical source, such as a battery, may be provided that is in communication with the electrodes, and a switch may alternately permit and cease to permit electrical current to flow from the electrical source to the electrodes. The switch may be controlled remotely. In other arrangements within the scope of the present disclosure, each ablation delivery catheter includes an optical fiber positioned to deliver a laser ablation signal to ablate tissue adjacent the mitral valve clip or anterior leaflet to allow for removal of the mitral valve clip or removal or alteration of the anterior leaflet. The transapical removal device may include an ablation source, such as a radiofrequency source, a laser source, or a cryo-thermal source. When the ablation source is a radiofrequency source, the radiofrequency signal may be in the range of 250-500 kHz. The snare head is controlled by a snare head controller connected at a proximal end of the delivery catheter. The snare head controller is configured to control the position and/or size of the snare basket during the deployed state and to control ablation source delivery to the tissue during the deployed state.

In some arrangements within the scope of the present disclosure, the transapical removal device comprises a grasping tool movable between a closed and open state and controlled by the snare head controller. The grasping tool is configured to allow manipulation of tissue or a mitral valve clip as needed. The grasping tool may be controllably movable by the snare head controller between a position inside a tube and a position outside the tube, and the snare head controller may control the movement of the grasping tool between the positions. The tube may be connected with or integral with the snare head.

In some arrangements within the scope of the present disclosure, the removal device includes a deployment mechanism for deploying a transcatheter valve into the mitral valve to replace a removed mitral valve clip. The deployment mechanism may comprise a delivery catheter, which contains the transcatheter valve and is configured to deliver, in a valve replacement mode, the transcatheter valve into the mitral valve to replace the removed mitral valve.

BRIEF DESCRIPTION OF THE DRAWINGS

FIG. 13 is an example block diagram 100 illustrating the various components used in implementing an example arrangement of a method of using a transapical removal device 102.

DETAILED DESCRIPTION

Figures 1A, 1B:
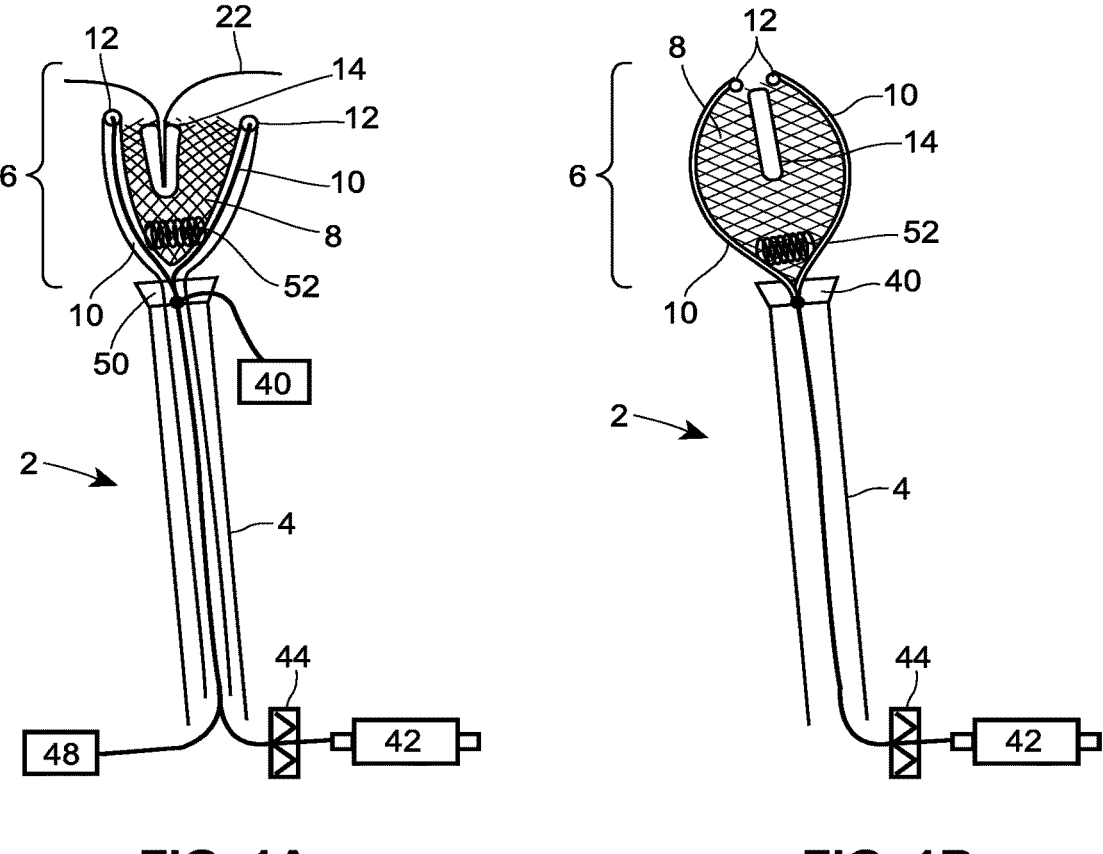
FIG. 1A illustrates a top view of a first arrangement of a transapical removal device of the present disclosure with the snare head in a deployed state.
FIG. 1B illustrates a top view of the first arrangement of the transapical removal device of FIG. 1A with the snare head in a collapsed state.

FIGS. 1A and 1B illustrate a first arrangement of a transapical removal device 2 of the present disclosure. The transapical removal device 2 includes a delivery catheter 4, a snare head 6, a snare basket 8, a spring 52, and ablation delivery catheters 10 with electrodes 12. An electrical source 42 and an ablation source 48 are in communication with the electrodes 12, and a switch 44 alternately permits and ceases to permit electrical current from the electrical source 42 to flow to the electrodes 12. In FIG. 1A, the snare head 6 and snare basket 8 are in a deployed state outside of the delivery catheter 4, and a mitral clip 14 is surrounded by the sides of the snare basket 8. The electrodes 12 of the ablation delivery catheters 10 are aligned with tissue of the heart that is to be ablated in order for the mitral clip 14 to be captured. For example, such tissue may be ablated when a control signal is provide to activate the ablation source 48 to provide an ablation signal, such as a radiofrequency signal, through the catheter 10 to ablate tissue of the mitral valve. FIG. 1B depicts the transapical removal device 2 after ablation has occurred and the mitral clip 14 has been captured by the snare basket 8. The snare head 6 is now in a collapsed configuration and can be removed from the heart, e.g., by being retracted through the delivery catheter 4. The transition of the snare head 6 between the collapsed state and the deployed sate is controlled by a snare head controller 40 connected at a proximal end of the delivery catheter 4. A retraction funnel 40 is provided to forcibly return the snare head to a collapsed state. The spring 52 is compressed when the snare head 6 is in the collapsed state and at rest when the snare head 6 is in the deployed state. For this catheter-based removal technique, the snare head 6 may apply pressure to the captured mitral valve clip 14 to collapse the clip down to a size or close to that of its initial size prior to deployment. This will allow the clip 14 to be removed through the catheter 4 more easily. It is noted that in some instances a slightly larger diameter delivery catheter 4 may be desired (in comparison to the original mitral valve clip delivery catheter) to compensate for tissue attached to the mitral valve clip 14 and ablated by the delivery catheters 10.

Figures 2A, 2B, 2C, 3A, 3B, 3C:
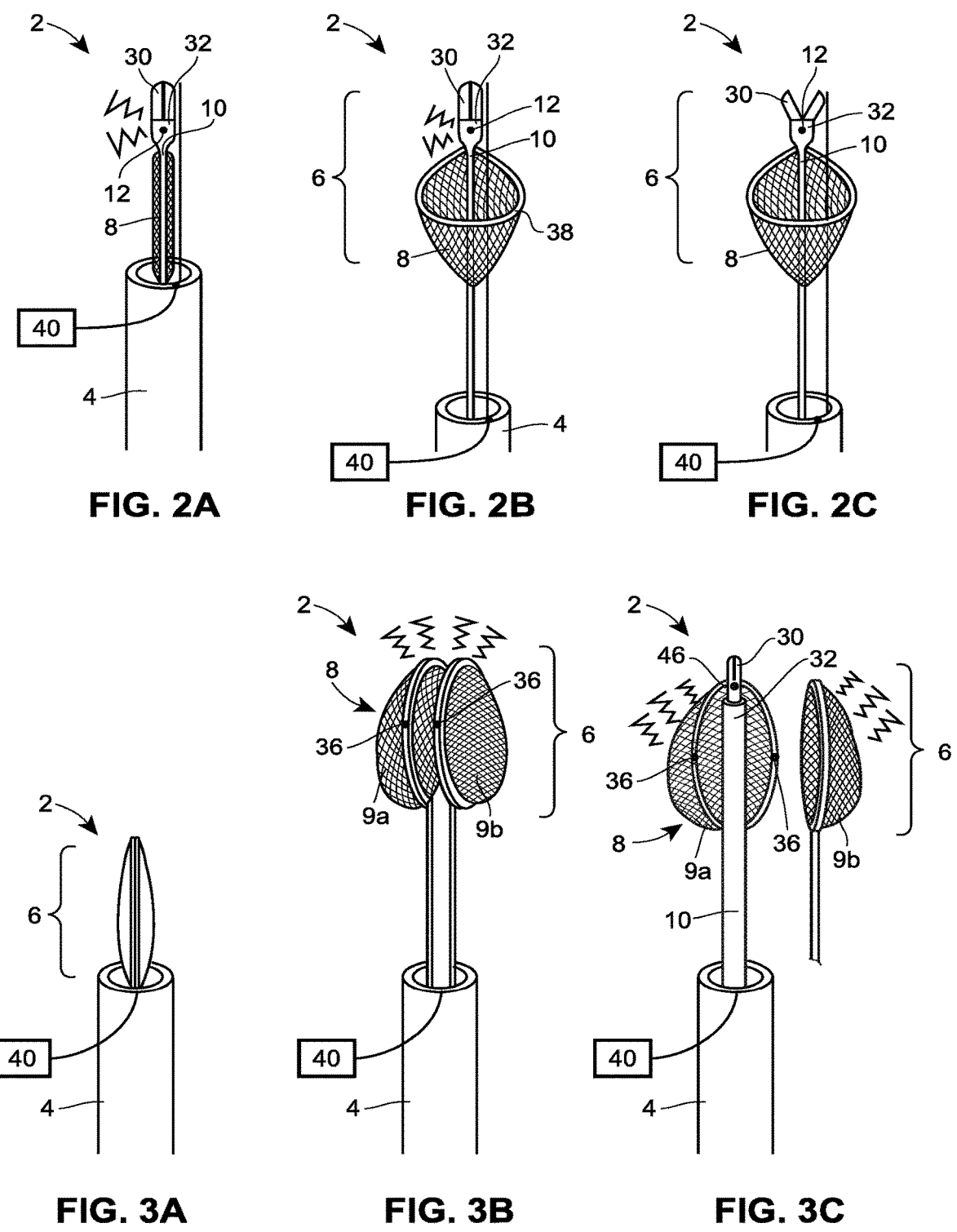
FIG. 2A illustrates an isometric side view of a second arrangement of a transapical removal device of the present disclosure with the snare head in a collapsed state wand a grasping tool of the snare head in a closed state.
FIG. 2B illustrates an isometric side view of the second arrangement of the transapical removal device of FIG. 2A with the snare head in a deployed state and the grasping tool of the snare head in a closed state.
FIG. 2C illustrates an isometric side view of the second arrangement of the transapical removal device of FIGS. 2A and 2B with the snare head in a deployed state and the grasping tool of the snare head in an open state.
FIG. 3A illustrates an isometric side view of a third arrangement of a transapical removal device of the present disclosure with a snare head in a collapsed state.
FIG. 3B illustrates an isometric side view of the third arrangement of the transapical transapical removal device of FIG. 3A with the snare head in a deployed state and the snare basket of the snare head in a closed state.
FIG. 3C illustrates an isometric side view of the third arrangement of the transapical removal device of FIGS. 3A and 3B with the snare head in a deployed state, the snare basket of the snare head in an open state, and a retractable grasping tool of the snare head in a closed state.

FIGS. 2A-2C illustrate a second arrangement of a transapical removal device 2 of the present disclosure. In addition to the elements discussed with respect to FIGS. 1A and 1B, the second arrangement of the transapcial removal device 2 includes a grasping tool 30 controllable by the snare head controller 40. The grasping tool 30 is movable between a closed state (shown in FIGS. 2A and 2B) and an open state (shown in FIG. 2C) and is configured to allow manipulation of tissue or the mitral valve clip as needed. The grasping tool 30 may be retractable such that it is controllably movable between a position inside a tube 32 and a position outside the tube 32. The snare basket 8 of the transapical removal device 2 depicted in FIGS. 2A-2C is closed by pulling on a cord 38, optionally using the grasping tool 30, in order to cinch the snare basket 8 closed.

FIGS. 3A-3C illustrate a third arrangement of a transapical removal device 2 of the present disclosure. The third arrangement of the transapical removal device 2 includes the elements disclosed with respect to the first and second arrangements. In the third arrangement of the transapical removal device 2, the snare head 6 has a two-part snare basket 8 having a first basket side 9a and a second basket side 9b. The third arrangement of the transapical removal device 2 allows the transapical removal device 2 to move between a collapsed state (shown in FIG. 3A), a deployed and closed state in which the first basket side 9a and the second basket side 9b are arranged to secure a mitral valve clip, tissue, or another element between them (shown in FIG. 3B), and a deployed and open state in which the first basket side 9a and the second basket side 9b are separated from one another, such as by being rotated to be at an angle relative to each other (shown in FIG. 3C). The first basket side 9a and the second basket side 9b have magnets 36 disposed on them that attract one another and thus facilitate moving the snare basket 8 to a closed state. In the third arrangement, ablation of heart tissue is achieved by an optical fiber 46.

Figure 4:
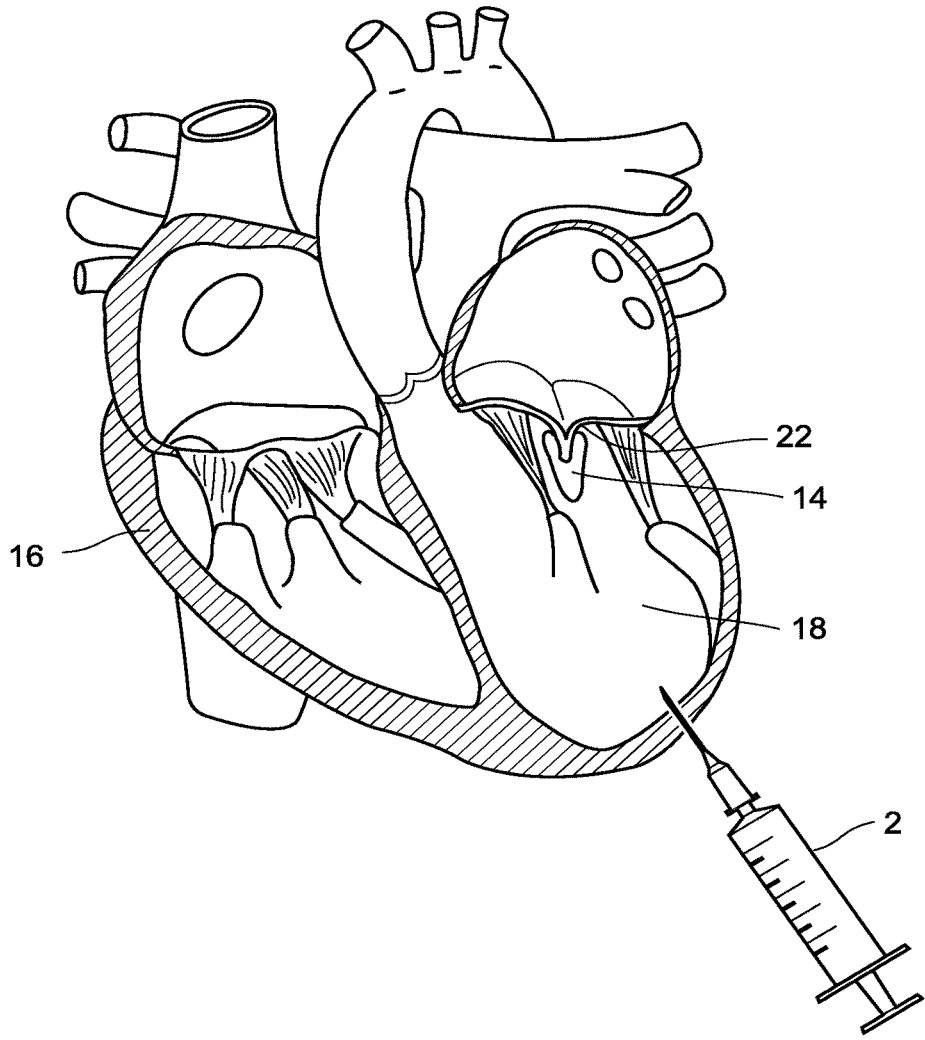
FIG. 4 illustrates a heart of a patient having a mitral clip at the mitral valve, wherein the transapical removal device of the present disclosure is being used to puncture the left ventricle of the heart.
Figure 5:
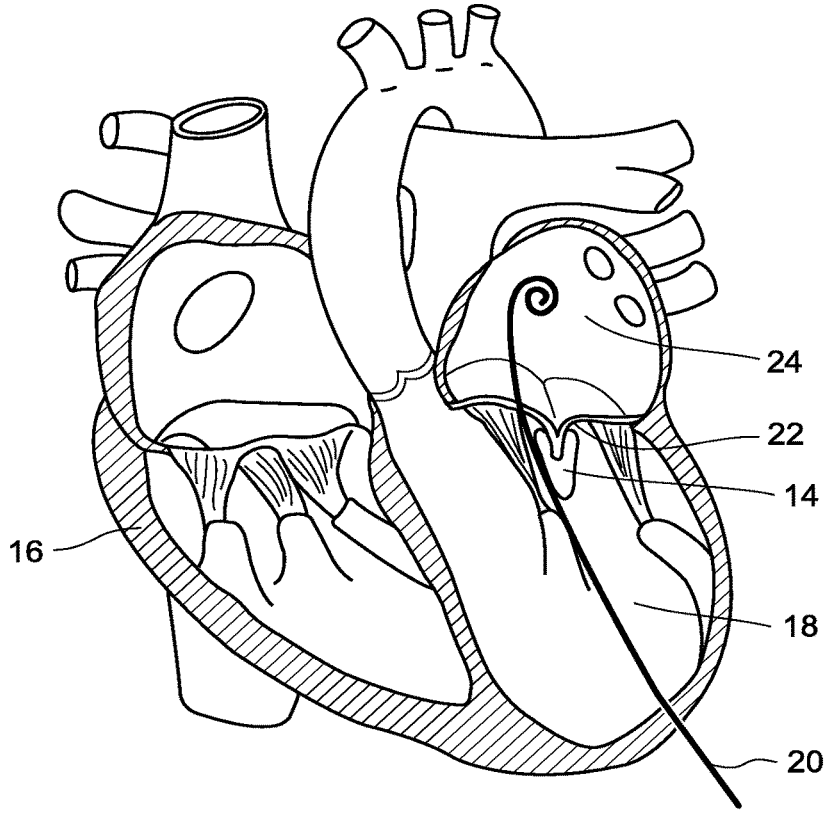
FIG. 5 illustrates the heart of the patient depicted in FIG. 4, wherein a guide wire of the transapical removal device of the present disclosure is being inserted through the puncture in the left ventricle, into the left ventricle, and up into the left atrium.
Figure 6:
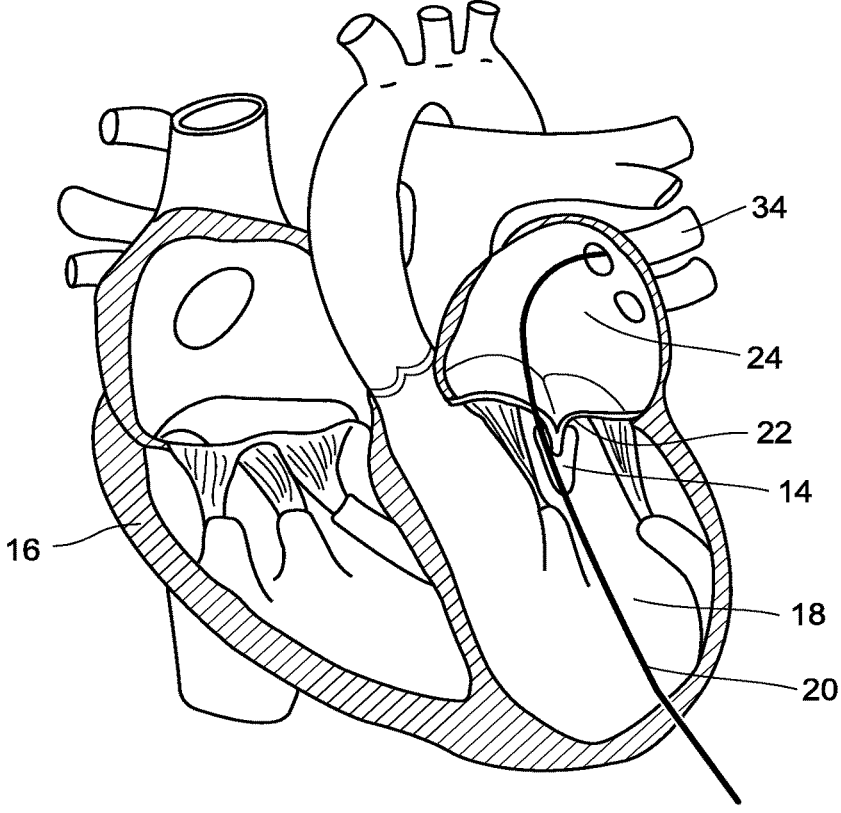
FIG. 6 illustrates the heart of the patient depicted in FIGS. 4 and 5, wherein a guide wire of the transapcial removal device of the present disclosure is being inserted into a pulmonary vein.
Figure 7:
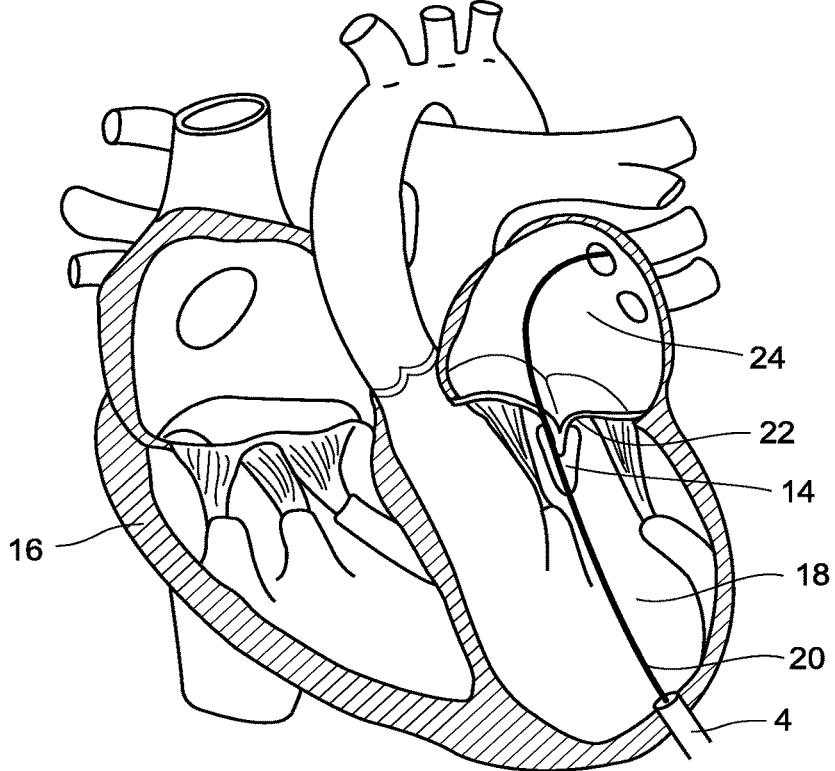
FIG. 7 illustrates the heart of the patient depicted in FIGS. 4-6, wherein a delivery catheter of the transapical removal device of the present disclosure is inserted into the left ventricle over the guide wire.
Figure 8:
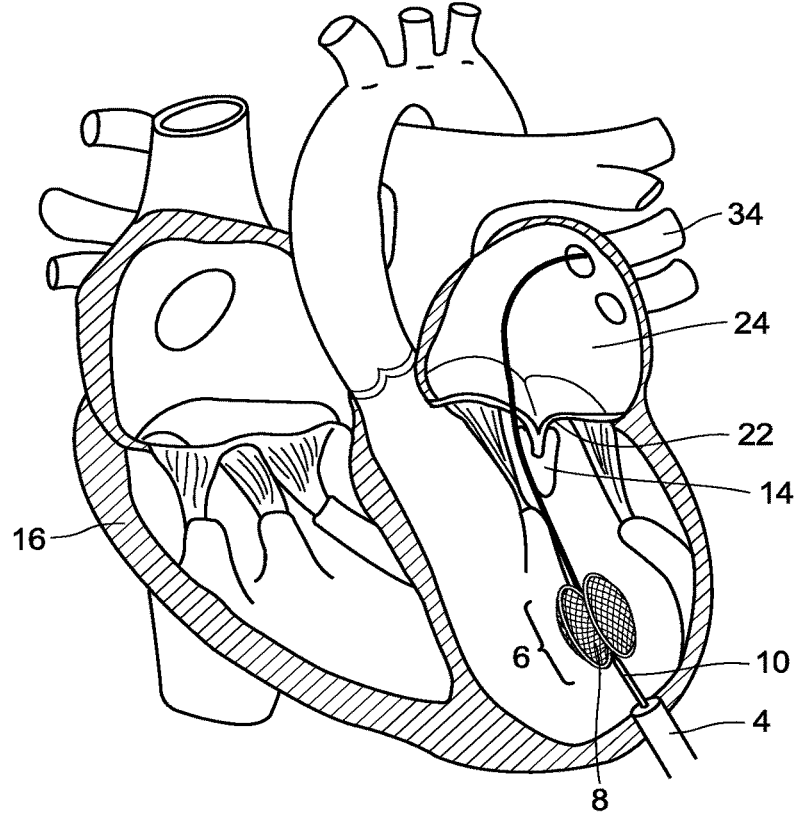
FIG. 8 illustrates the heart of the patient depicted in FIGS. 4-7, wherein a snare head is deployed from the delivery catheter.
Figure 9:
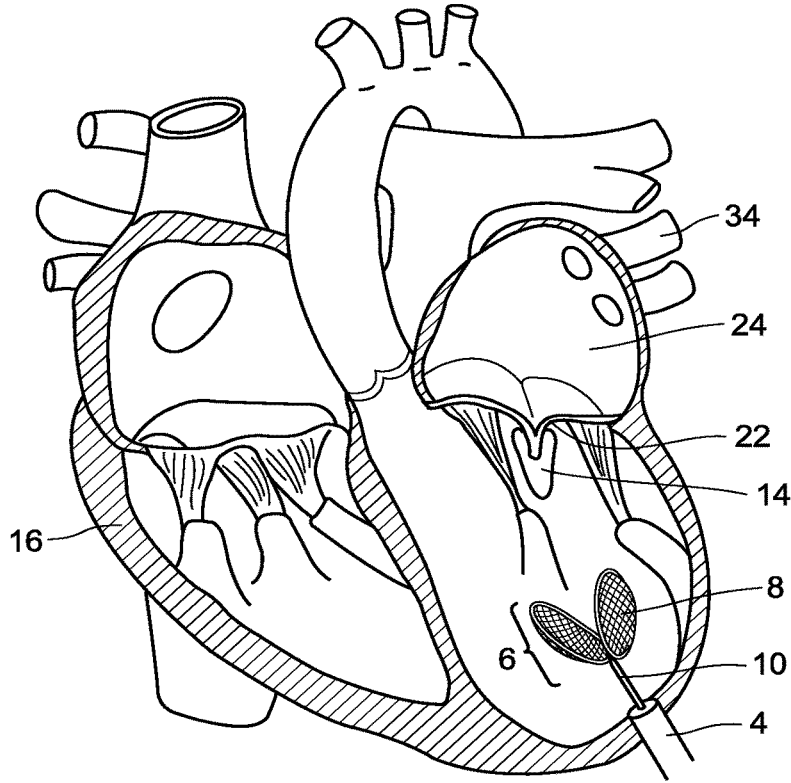
FIG. 9 illustrates the heart of the patient depicted in FIGS. 4-8, wherein the snare head is opened so that it can surround the mitral clip.
Figure 10:
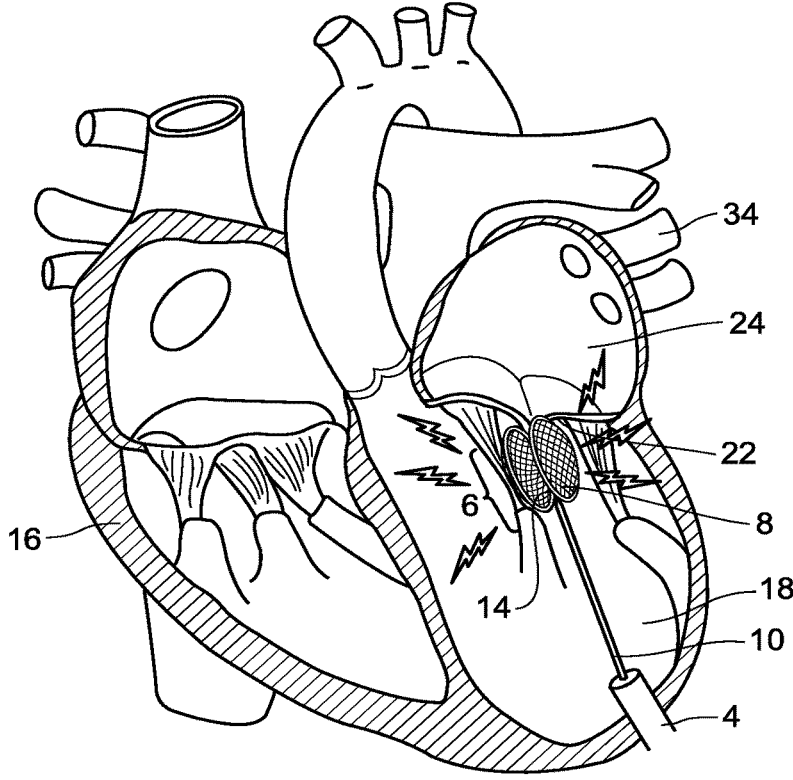
FIG. 10 illustrates the heart of the patient depicted in FIGS. 4-9, wherein the snare head is closed around the mitral clip, the tissue surrounding the mitral clip is ablated, and the mitral clip is captured in the snare head.

FIGS. 4-12 depict a transapical method of removing a mitral valve clip 14. This method could also be used to remove or alter an anterior leaflet of the mitral valve. In FIG. 4, a mitral valve clip 14 that has been pre-positioned on the mitral valve 22 to bind at least a portion of the mitral valve is depicted in a heart 16 of a patient. The transapical removal device 2 is used to puncture the left ventricle 18 of the heart 16. As shown in FIG. 5, a guide catheter 20 is then inserted into the left ventricle, through the mitral valve 22, and into the left atrium 24. As shown in FIG. 6, the guide catheter 20 may be inserted into a pulmonary vein 34. As shown in FIG. 7, using the guide catheter 20, the delivery catheter 4 is inserted into the left ventricle 18. As shown in FIG. 8, the snare head 6 is deployed from a collapsed state that allowed it to move through the delivery catheter 4 to a deployed state that allows it to capture the mitral valve clip 14. A snare head controller (not pictured) controls the transition of the snare head between the collapsed state and the deployed state. As shown in FIG. 9, the snare head 6 has a snare basket 8 that opens to at least partially surround the pre-positioned mitral valve clip 14. The snare basket may include medical-grade plastic, medical-grade metal, or both. In some arrangements within the scope of the present disclosure, the snare head 6 may be made from a shape memory material such as nitinol in order to assist with deployment of the snare head 6. In other arrangements within the scope of the present disclosure, such as that shown in FIGS. 1A and 1B, the snare head 6 may include a spring that is compressed when the snare head 6 is in the collapsed state and at rest when the snare head 6 is in the deployed state, the spring configured to be compressed within the snare basket 8 unless the snare basket 8 is in the deployed state. As shown in FIG. 10, the snare basket 8 then closes around the mitral valve clip 14. In some arrangements, the snare head 6 may include magnets 36 (shown in FIGS. 3B and 3C) that cause the snare head basket 8 to close.

Once the snare basket is closed around the mitral valve clip 14, an ablation signal is provided to the ablation delivery catheters 10 and delivered to the tissue surrounding the mitral valve clip 14. In some arrangements within the scope of the present disclosure, the ablation delivery catheters 10 each have an electrode 12 provided on a proximal end for supplying radiofrequency energy to ablate tissue. The radiofrequency signal may be in the range of 250-500 kHz. An electrical source 42 (shown in FIGS. 1A and 1B) such as a battery, can be in communication with the electrodes 12, and a switch 44 may be provided that alternately permits and ceases to permit electrical current to flow from the electrical source to the electrodes. The switch may be controlled remotely. In other arrangements within the scope of the present disclosure, an optical fiber 46 (shown in FIG. 3C) is positioned at a proximal end of each ablation delivery catheter 10 to deliver a laser ablation signal to ablate tissue adjacent the mitral valve clip 14. In other arrangements, the ablation source may be a cryo-thermal source.

Figure 11:
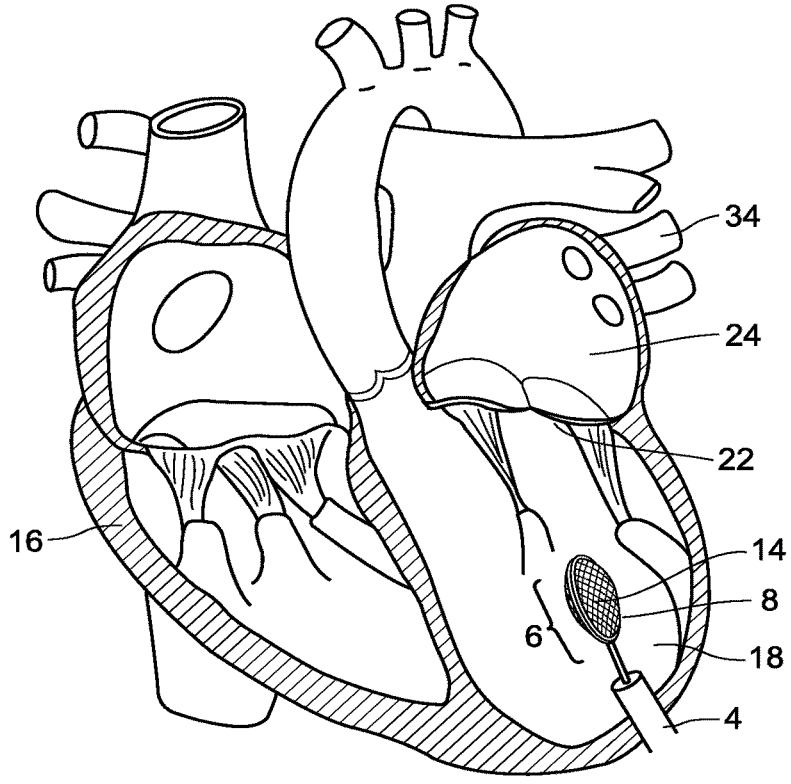
FIG. 11 illustrates the heart of the patient depicted in FIGS. 4-10, wherein the snare head is in a collapsed state after capturing the mitral clip.
Figure 12:
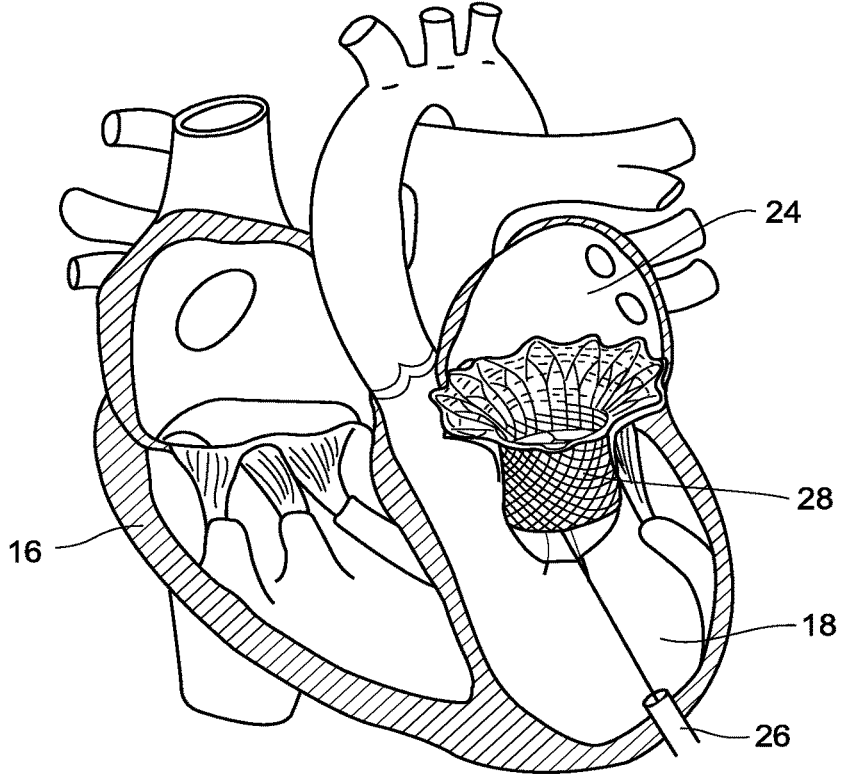
FIG. 12 illustrates the heart of the patient depicted in FIGS. 4-11, wherein a new transcatheter valve is deployed into the mitral valve through the delivery catheter.

The snare head controller controls the position and/or size of the snare basket 8 during the deployed state and also controls ablation source delivery to the tissue during the deployed state. The mitral valve clip 14 is then captured by the snare basket 8 of the snare head 6. As shown in FIG. 11, the snare head 6 assumes a collapsed state and is retracted into the delivery catheter 4. In some arrangements within the scope of the present disclosure, a retraction funnel (shown in FIGS. 1A and 1B) may be provided at a proximal end of the delivery catheter 4 to help forcibly return the snare head 6 to the collapsed state from the deployed state. In order to provide a functional mitral valve 22, a new transcatheter valve 28 may be deployed by a deployment mechanism 26, which includes the delivery catheter 4 in the arrangement depicted in FIG. 12.

Although the method of using a transapical removal device 2 depicted in FIGS. 4-12 is directed to removal of a mitral valve clip 14, the transapical removal device 2 could be used for other purposes, such as to remove or alter the anterior leaflet. A person having skill in the art would recognize that substantially the same steps as discussed above could be used for such purposes. Although the snare basket 8 is depicted as having a two-part snare basket in FIGS. 4-12, a single-part basket or a multi-part basket having more than two sides may be used. Further, the snare basket 8 may be configured in a variety of shapes may. For example, the snare basket 8 may be open-ended at its distal and proximal ends for slidable removal of the captured tissue and/or clip, once the assembly is fully extracted from the subject. In other examples, the snare basket 8 may be continuous or otherwise sealed at the distal and proximal ends. In some examples, the snare basket 8 may have a flat configuration that facilitates removal or alteration of the anterior leaflet. In yet other examples, the ablation delivery catheters 10 may be secured to the snare basket 8 in a way that allows ablation of only a portion of an anterior leaflet, such as the center portion.

Figure 13:
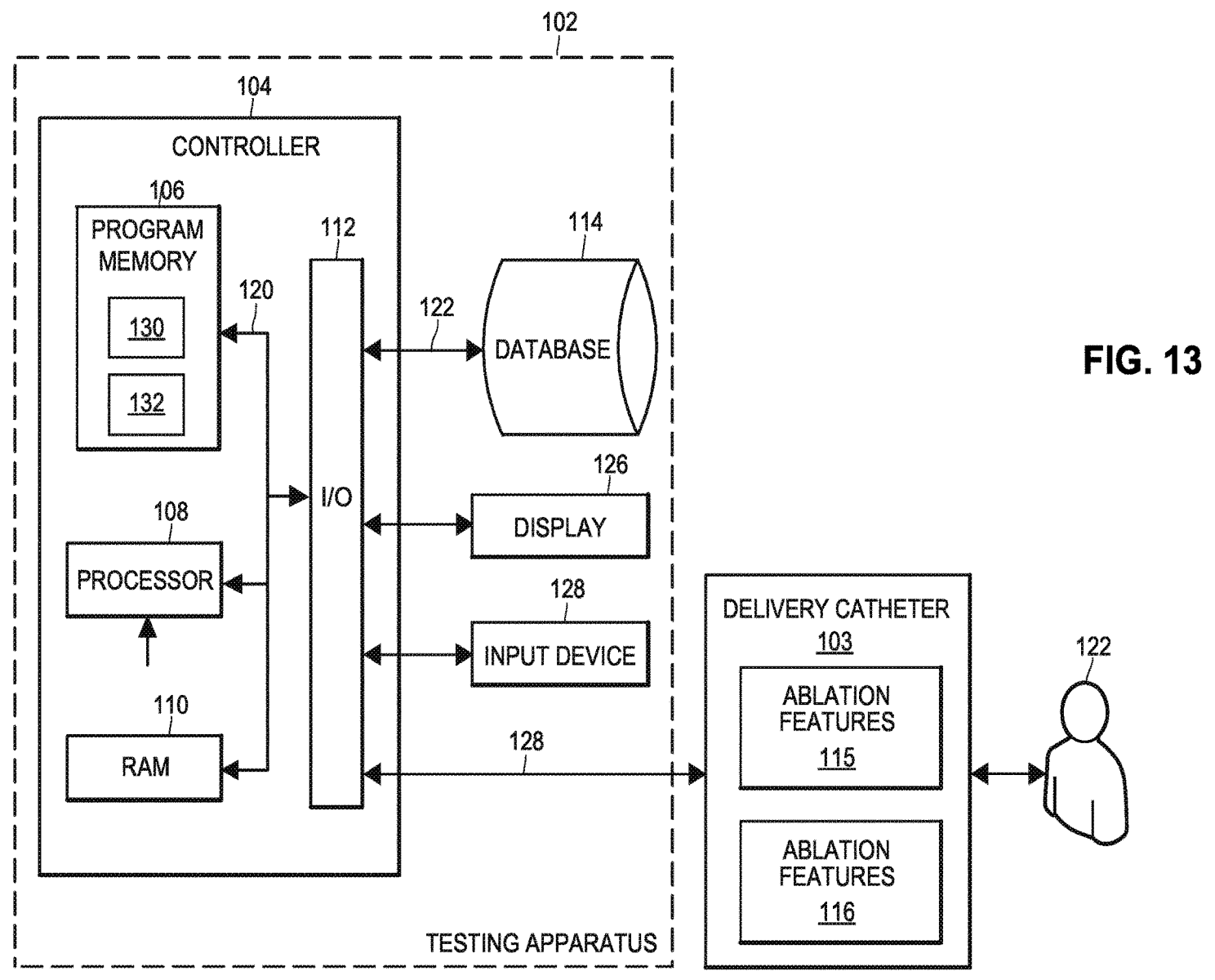

FIG. 13 is an example block diagram 100 illustrating the various components used in implementing an example arrangement of a method of using a transapical removal device as discussed herein. A transapical removal device may be inserted into a patient 122 via a delivery catheter 103 that may include ablation features 115 and sensors 116. The removal device may be controlled by a control system 102 having a snare head controller 104 operatively connected to various elements of the system 102. The control system 102 may be a standalone transapical device removal system, such as a portable machine at a point of care position. In other examples, the control system 102 may be implemented into existing control systems, such as an existing ablation control system, having an ablation pump, a catheter sensor/switching control system, etc. While not shown, the control system 102 may include mechanical controls, such as foot controls and hand controls for providing full or partial mechanical operation of catheter delivery, snare head deployment, and ablation features. It will be appreciated that some portion of the control system 102, whether electronic and/or mechanical portions, may be distributed into a control handle for the delivery catheter of the removal device, for snare head, sensor, and/or catheter control.

In the illustrated example, the control system 102 includes a database 114 (via a link 122 connected to an input/output (I/O) circuit 112) for storing collect data, such as historical data from the controller 104 and/or from external data sources, such as historical data collected from other medical devices and medical databases. That is, it should be noted that, while not shown, additional databases may be linked to the snare head controller 104 in a known manner.

The snare head controller 104 includes a program memory 106, the processor 108 (may be called a microcontroller or a microprocessor), a random-access memory (RAM) 110, and the input/output (I/O) circuit 112, all of which are interconnected via an address/data bus 120. It should be appreciated that although only one microprocessor 108 is shown, the snare head controller 104 may include multiple microprocessors 108. Similarly, the memory of the controller 104 may include multiple RAMs 110 and multiple program memories 106. Although the I/O circuit 112 is shown as a single block, it should be appreciated that the I/O circuit 112 may include a number of different types of I/O circuits. The RAM(s) 110 and the program memories 106 may be implemented as semiconductor memories, magnetically readable memories, and/or optically readable memories, for example. A link 124 may operatively connect the controller 104 to the sensors 116 through the I/O circuit 112.

The program memory 106 and/or the RAM 110 may store various applications (i.e., machine readable instructions) for execution by the microprocessor 108. For example, an operating system 130 may generally control the operation of the control system 102 and provide a user interface to the control system 102 to implement the removal processes described herein. The program memory 106 and/or the RAM 110 may also store a variety of subroutines 132 for accessing specific functions of the testing apparatus 102. By way of example, and without limitation, the subroutines 132 may include, among other things: a subroutine for controlling ablation of mitral valve tissue, a subroutine for controlling activation of a snare head from a first collapsed state for delivery to the mitral value, to a deployed state for snaring the mitral valve clip, and then to a second collapsed state for removing the capture mitral valve clip, as well as other subroutines, for example, implementing software keyboard functionality, interfacing with other hardware in the computer system 102, etc. The program memory 106 and/or the RAM 110 may further store data related to the configuration and/or operation of the transapical removal device, and/or related to the operation of one or more subroutines 132. In addition to the controller 104, the control system 102 may include other hardware resources.

The control system 102 may also include various types of input/output hardware such as a visual display 126 and input device(s) 128 (e.g., keypad, keyboard, etc.). In an arrangement, the display 126 is touch-sensitive, and may cooperate with a software keyboard routine as one of the software routines 132 to accept user input. It may be advantageous for the testing apparatus to communicate with broader medical analysis networks or medical treatment networks (not shown) through any of a number of known networking devices and techniques (e.g., through a commuter network such as a hospital or clinic intranet, the Internet, etc.). For example, the control system 102 may be connected to a medical records database, hospital management processing system, health care professional terminals (e.g., doctor stations, nurse stations), patient monitoring systems, automated drug delivery systems. Accordingly, the disclosed arrangements may be used as part of an automated closed loop system or as part of a decision assist system.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain arrangements are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example arrangements, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various arrangements, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering arrangements in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In arrangements in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example arrangements, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example arrangements, the processor or processors may be located in a single location (e.g., within a home environment, an office environment or as a server farm), while in other arrangements the processors may be distributed across a number of locations.

The performance of certain of the operations may be distributed among the one or more processors, not only residing within a single machine, but deployed across a number of machines. In some example arrangements, the one or more processors or processor-implemented modules may be located in a single geographic location (e.g., within a home environment, an office environment, or a server farm). In other example arrangements, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

Some arrangements may be described using the expression "coupled" and "connected" along with their derivatives. For example, some arrangements may be described using the term "coupled" to indicate that two or more elements are in direct physical or electrical contact. The term "coupled," however, may also mean that two or more elements are not in direct contact with each other, but yet still co-operate or interact with each other. The arrangements are not limited This detailed description is to be construed as examples and does not describe every possible arrangement, as describing every possible arrangement would be impractical, if not impossible. One could implement numerous alternate arrangements, using either current technology or technology developed after the filing date of this application.

As used herein any reference to "one arrangement" or "an arrangement" means that a particular element, feature, structure, or characteristic described in connection with the arrangement is included in at least one arrangement. The appearances of the phrase "in one arrangement" in various places in the specification are not necessarily all referring to the same arrangement.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the arrangements herein. This is done merely for convenience and to give a general sense of the description. This description, and the claims that follow, should be read to include one or at least one and the singular also includes the plural unless it is obvious that it is meant otherwise.

While the present invention has been described with reference to specific examples, which are intended to be illustrative only and not to be limiting of the invention, it will be apparent to those of ordinary skill in the art that changes, additions and/or deletions may be made to the disclosed arrangements without departing from the spirit and scope of the invention.

The foregoing description is given for clearness of understanding; and no unnecessary limitations should be understood therefrom, as modifications within the scope of the invention may be apparent to those having ordinary skill in the art.

11

12

What is claimed:

1. A method to remove a valve clip pre-positioned on a heart valve leaflet comprising:

delivering, to a chamber of a heart, a removal device, the removal device comprising:

a delivery catheter having a distal end portion configured to be positioned near a heart valve, a grasping tool deployable from the distal end portion of the delivery catheter, the grasping tool configured to be moveable between an open state and a closed state to grasp and manipulate the valve clip, and a removal tool extendable relative the distal end portion of the delivery catheter, the removal tool configured to at least partially surround the valve clip and to remove the valve clip from the heart valve leaflet;

deploying the grasping tool from the open state to the closed state to grasp a first portion of the valve clip;

at least partially surrounding the valve clip with the removal tool;

collapsing the valve clip for removal from the heart; and removing the valve clip from the heart valve leaflet using the removal tool.

2. The method of claim 1, wherein the grasping tool is movable between an open state and a closed state, the grasping tool includes a grasping element disposed within an actuation tube deployable from the distal end of the delivery catheter, and wherein deploying the grasping tool comprises moving the grasping element outside the actuation tube to move the grasping tool from the closed state to the open state.

3. The method of claim 1, wherein the removal tool comprises a snare basket, and at least partially surrounding the valve clip comprising positioning the snare basket to at least partially surround the valve clip.

4. The method of claim 3, wherein the snare basket has an open distal end to receive the valve clip, and wherein the method further comprises cinching the snare basket around the valve clip.

5. The method of claim 3, wherein the snare basket comprises a first side and a second side moveable relative each other, and at least partially surrounding the valve clip comprises capturing the valve clip between the first side and the second side.

6. The method of claim 1, further comprising removing the valve clip through the delivery catheter when the valve clip is in a collapsed state using the removal tool.

7. The method of claim 1, wherein the removal tool comprises an ablation device, and further wherein removing the valve clip from the heart valve leaflet comprises ablating the heart valve leaflet using the ablation device.

8. The method of claim 7, wherein ablating the heart valve leaflet comprises delivering radiofrequency energy to the heart valve leaflet using the ablation device.

9. The method of claim 7, wherein ablating the heart valve leaflet comprises delivering a laser ablation signal to the heart valve leaflet using the ablation device.

10. A method of removing a valve clip pre-positioned on a leaflet of a heart valve of a heart comprising:

guiding a delivery catheter to the heart valve;

grasping the valve clip with a grasping tool extending from the delivery catheter;

deploying a snare basket of a snare head from the delivery catheter and from a collapsed state to a deployed state such that the snare basket at least partially surrounds the valve clip;

surrounding the valve clip with the snare basket;

ablating the valve leaflet with an ablation device extending from the delivery catheter while the grasping tool continues to grasp the valve clip and while the valve clip is surrounded by the snare basket; and removing the valve clip from the heart.

11. The method of claim 10, wherein the surrounding step includes closing an end of the snare basket.

12. The method of claim 10, wherein the removing step includes retracting the snare basket with the valve clip into the distal end of the clip removal device.

13. The method of claim 10, wherein the ablating step includes removing at least a portion of the leaflet.

14. The method of claim 10, wherein the snare basket includes a first basket side and a second basket side, and the closing step includes bringing the first and second basket sides together over the valve clip.

15. The method of claim 10, wherein the snare basket includes a closed end and an open end, the open end extending continuously about the grasping tool when in the deployed state, and the closing step includes cinching the open end from an open state to a closed state.

16. The method of claim 15, wherein the at least one electrode is connected to the snare basket, and the ablating step includes emitting ablation energy from the at least one electrode connected to the snare basket to the leaflet.

17. The method of claim 15, wherein the at least one electrode is connected to the grasping tool, and the ablating step includes emitting ablation energy from the at least one electrode connected to the grasping tool to the leaflet.

18. The method of claim 10, wherein the ablation device includes at least one electrode configured to emit ablation energy therefrom.

19. The method of claim 10, wherein the heart valve is a mitral valve, and the guiding step includes transapically passing the delivery catheter into the left ventricle.

20. The method claim 10, wherein the snare basket is biased toward a radially expanded state, the deploying step includes advancing the snare basket from the delivery catheter such that the snare basket expands radially outwardly under its own bias to the deployed state, and the removing step includes retracting the snare basket within the delivery catheter such that the snare basket collapses back to the collapsed state.

21. The method of claim 20, wherein the snare basket is made from a shape memory material.

* * * * *